(12) United States Patent
Lupia

(10) Patent No.: US 11,103,390 B2
(45) Date of Patent: Aug. 31, 2021

(54) SANITARY NAPKIN DISPOSAL DEVICE

(71) Applicant: Mario Lupia, Staten Island, NY (US)

(72) Inventor: Mario Lupia, Staten Island, NY (US)

(*) Notice: Subject to any disclaimer, the term of this patent is extended or adjusted under 35 U.S.C. 154(b) by 0 days.

(21) Appl. No.: 16/777,106

(22) Filed: Jan. 30, 2020

(65) Prior Publication Data

US 2020/0237583 A1 Jul. 30, 2020

Related U.S. Application Data

(60) Provisional application No. 62/798,542, filed on Jan. 30, 2019.

(51) Int. Cl.
  *A61F 13/551* (2006.01)
  *A61F 13/84* (2006.01)
  *B65G 11/20* (2006.01)
  *B65F 1/14* (2006.01)

(52) U.S. Cl.
  CPC .......... *A61F 13/5515* (2013.01); *A61F 13/84* (2013.01); *B65F 1/1431* (2013.01); *B65G 11/203* (2013.01); *A61F 2013/8402* (2013.01); *B65F 2210/148* (2013.01); *B65F 2240/164* (2013.01)

(58) Field of Classification Search
  CPC .................. A61F 13/5515; A61F 13/84; A61F 2013/8402; B65F 1/1431; B65F 2240/164; B65F 2210/148; B65F 1/1615; B65F 7/00; B65F 1/10; B65F 11/203
  See application file for complete search history.

(56) References Cited

U.S. PATENT DOCUMENTS

| 814,563 | A | * | 3/1906 | Pond ........................ B65F 1/10 |
| 2,281,630 | A | * | 5/1942 | Southard .................. B65F 7/00 |
| | | | | 220/87.2 |
| 4,694,947 | A | * | 9/1987 | Nineberg ................ F23G 5/444 |
| | | | | 110/116 |
| 5,154,345 | A | * | 10/1992 | Shillington ......... A61M 5/3205 |
| | | | | 206/366 |
| 6,120,743 | A | * | 9/2000 | Papari ....................... A61L 2/18 |
| | | | | 206/438 |
| 7,490,731 | B2 | | 2/2009 | Hautop |
| 2005/0263575 | A1 | | 12/2005 | Weinmann |
| 2006/0045391 | A1 | | 3/2006 | Reglar |
| 2007/0295722 | A1 | * | 12/2007 | Titas ....................... B65F 1/141 |
| | | | | 220/23.83 |
| 2009/0184125 | A1 | * | 7/2009 | Brown .................. B65F 1/0006 |
| | | | | 220/502 |
| 2013/0146501 | A1 | * | 6/2013 | Zusmanis ............. B65F 1/1638 |
| | | | | 206/525 |

(Continued)

*Primary Examiner* — Mark A Deuble
(74) *Attorney, Agent, or Firm* — Boudwin Intellectual Property; Daniel Boudwin

(57) ABSTRACT

A sanitary napkin disposal device. The sanitary napkin disposal device includes a housing. The housing is defined by a base, where a plurality of sidewalls extends upward from the base towards a top wall. This housing defines an interior volume. An opening extends through a sidewall of the housing and provides access to the interior volume of the housing. The opening feeds into a chute, such that items placed through the opening will fall into the chute. A door is placed over the opening, the door is movable between an open position and a closed position. The door is spring-biased in a closed position.

13 Claims, 5 Drawing Sheets

(56) References Cited

U.S. PATENT DOCUMENTS

| | | | |
|---|---|---|---|
| 2014/0054293 A1* | 2/2014 | Goodfield | B65F 1/1426 |
| | | | 220/495.06 |
| 2014/0117114 A1* | 5/2014 | Muderlak | B65F 1/1638 |
| | | | 239/274 |
| 2015/0239664 A1 | 8/2015 | Liistro et al. | |
| 2017/0240353 A1* | 8/2017 | Schuur | B65F 1/10 |
| 2018/0057257 A1* | 3/2018 | Campbell | B65F 1/068 |
| 2019/0270586 A1* | 9/2019 | Lovingood | B65F 1/1638 |

\* cited by examiner

SANITARY NAPKIN DISPOSAL DEVICE

CROSS REFERENCE TO RELATED APPLICATIONS

This application claims the benefit of U.S. Provisional Application No. 62/798,542 filed on Jan. 30, 2019. The above identified patent application is herein incorporated by reference in its entirety to provide continuity of disclosure.

BACKGROUND OF THE INVENTION

The present invention relates to a sanitary napkin disposal device. The disposal of sanitary napkins and other feminine products can be a difficult issues. Specifically, when disposing of such products in a public restroom, a woman may find the process difficult, unsanitary, unsightly and potentially embarrassing. Many public restrooms are not equipped with a disposal system for used sanitary napkins and feminine products. Those that do include a disposal system are often unsatisfactory, as these systems typically still rely on individuals manually cleaning them out at regular intervals.

In addition to being inconvenient and questionable in effectiveness, most current systems are also unsanitary in nature. When used sanitary napkins and feminine products are discarded, they typically include biological materials that can be known to spread germs and diseases. This unsanitary nature can be cause by overuse of the disposal system, limited maintenance to the disposal system or improper use by individuals using the disposal system.

Therefore, there is a defined need amongst the known art references for a device that will allow for the safe and sanitary disposal of sanitary napkins or other used feminine products.

SUMMARY OF THE INVENTION

In view of the foregoing disadvantages inherent in the known types of feminine product disposal devices now present in the prior art, the present invention provides a sanitary napkin disposal device wherein the same can be utilized for providing convenience for the user when disposing of used feminine products in a safe and sanitary manner.

The present system comprises a housing. The housing is defined by a plurality of sidewalls that extend upward from a base before making contact with a top wall. This housing defines an interior volume. An opening is disposed on the housing, through a sidewall thereof, providing access to the interior volume. The opening of the housing feeds into a chute. A door is disposed over the opening, such that the door can be moved between an open position and a closed position.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
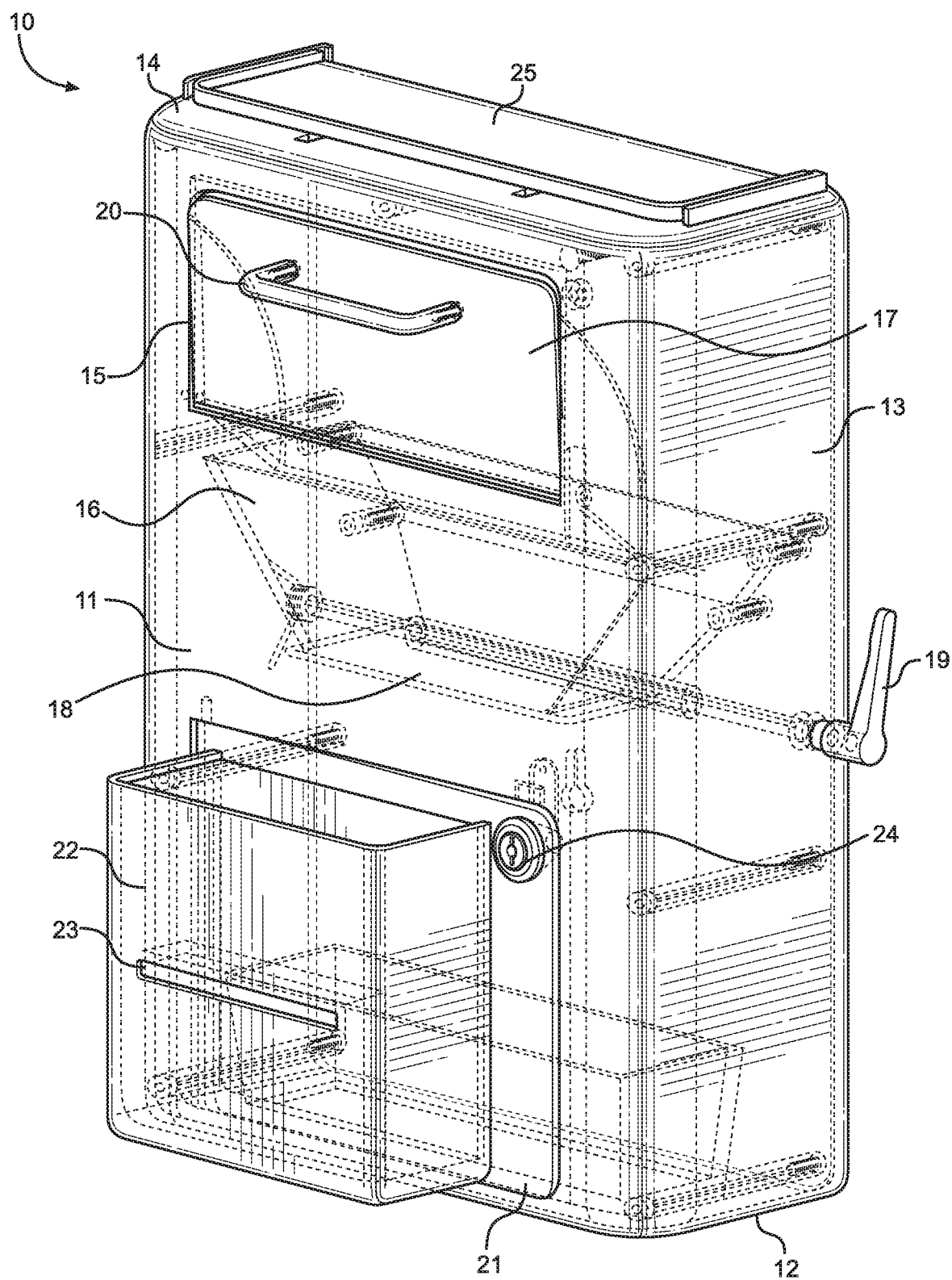
FIG. 1 shows a perspective view of an embodiment of the sanitary napkin disposal device.

Reference is made herein to the attached drawings. Like reference numerals are used throughout the drawings to depict like or similar elements of the Sanitary Napkin Disposal Device. The figures are intended for representative purposes only and should not be considered to be limiting in any respect.

Referring now to FIG. 1, there is shown a perspective view of an embodiment of the sanitary napkin disposal device. The sanitary napkin disposal device 10 comprises a housing 11. The housing 11 is defined by a base 12 with a plurality of sidewalls 13 extending upward therefrom. In the illustrated embodiment, the plurality of sidewalk 13 consists of four sidewalls with a rear sidewall opposite a front sidewall and a pair of opposing side sidewalls. Furthermore, in the illustrated embodiment, the plurality of sidewalls 13 are adjoined such that the housing 11 defines rounded corners and edges. The plurality of sidewalls 13 extend upward from the base 12 before terminating at a top wall 14. In the illustrated embodiment, the top wall 14 is of an identical perimeter to the base 12, such that the housing 11 is of an identical perimeter from the base 12 to the top wall 14. The housing 11 defines an interior volume. The housing 11 is made of any suitable material, such as plastic or metal. Furthermore, the housing 11 may be airtight or liquid-tight, such that fluids or contaminants will not be able to exit the housing 11 once they are placed therein.

An opening 15 is disposed on the housing 11, providing access to the interior volume. Specifically, in the illustrated embodiment, the opening 15 is disposed on an upper portion of the front sidewall of the plurality of sidewalls 13. The opening 15 is, ideally, disposed on an upper portion of the plurality of sidewalls 13, such that disposed items can be guided to a lower portion of the plurality of sidewalls 13.

A chute 16 is in operable connection with the opening 15, such that items placed through the opening 15 will enter the chute 16. As shown, the chute 16 comprises an upper opening in a vertical opposition to a lower opening. The upper opening of the chute 16 is of a greater perimeter than the lower opening of the chute 16. The chute 16 further comprises a plurality of slanted walls extending between the upper opening of the chute 16 and the lower opening of the chute 16.

A door 17 is disposed on the housing over the opening 15. The door 17 is movable between an open position (shown in FIG. 2) and a closed position, as shown. As such, the user must place the door 17 into the open position in order to place disposed items therethrough. The door 17 is spring-biased in the closed position, such as to prevent the spread of germs or contaminants from the interior volume of the housing 11. The door 17 may be spring-biased by any means, such as by a spring coil. Furthermore, in the illustrated embodiment, the door 17 is inset on the front sidewall of the plurality of sidewalls 13, such that when the door 17 is in the closed position, it rests flush with the plurality of sidewalls 13. In some embodiments, the door 17 comprises a handle 20 thereon, such that the user can utilize the handle 20 to move the door 17 between the open position and the closed position.

In the illustrated embodiment, the chute 16 comprises a trap door 18. The trap door 18 is movable between a closed position and an open position. The closed position is defined where trap door 18 covers the lower opening of the chute 16, such that disposed items will rest on top of the trap door 18 when placed through the opening 15 of the housing 11. The trap door 18 is spring-biased in a closed position, such that the upward character of the closed position is maintained. The trap door 18 is movable between the closed position into the open position via a trap door handle 19 disposed on an external surface of the housing 11. In the illustrated embodiment, the trap door handle is disposed on a side sidewall of the pair of opposing sidewalk. The trap door handle 19 is pointed upward when in the closed position, such when the user pulls the trap door handle 19 into a horizontal position, the trap door 18 will move into the open position.

In some embodiments, the sanitary napkin disposal device 10 comprises a waste door 21. The waste door 21 provides access to the interior volume of the housing 11. In the illustrated embodiment, the waste door 21 is disposed on a bottom portion of the front wall of the plurality of sidewalls 13 of the housing 11. The waste door 21 is positioned below the opening 15. Additionally, in the illustrated embodiment, the waste door 21 comprises a box 22 on a front surface thereof. The box 22 comprises a slot 23, such that the box 22 can be used to store items and the slot 23 can be used to access those items. For example, the box 22 can be utilized to store wax papers, tissues or toilet covers. The box 22 can be of any size for a desired function, however, the box 22 is fully contained within the perimeter of the waste door 21. Furthermore, in some embodiments, the waste door 21 comprises a lock 24 thereon. The lock 24 is positioned in an upper corner of the waste door 21 and is configured to hold the waste door 21 in the closed position.

In the illustrated embodiment, an extendable platform 25 is disposed on the top wall 14 of the housing 11. The extendable platform 25 is configured to secure items placed thereon. For example, the user may desire to place an item, such as a cellular phone on the extendable platform 25 while using the restroom. The extendable platform 25 is movable between a stored position (shown in FIG. 1) and a deployed position (shown in FIG. 2) by an means. For example, the extendable platform 25 may be movable between a stored position and a deployed position by a lateral sliding mechanism or by a folding mechanism.

Figure 2:
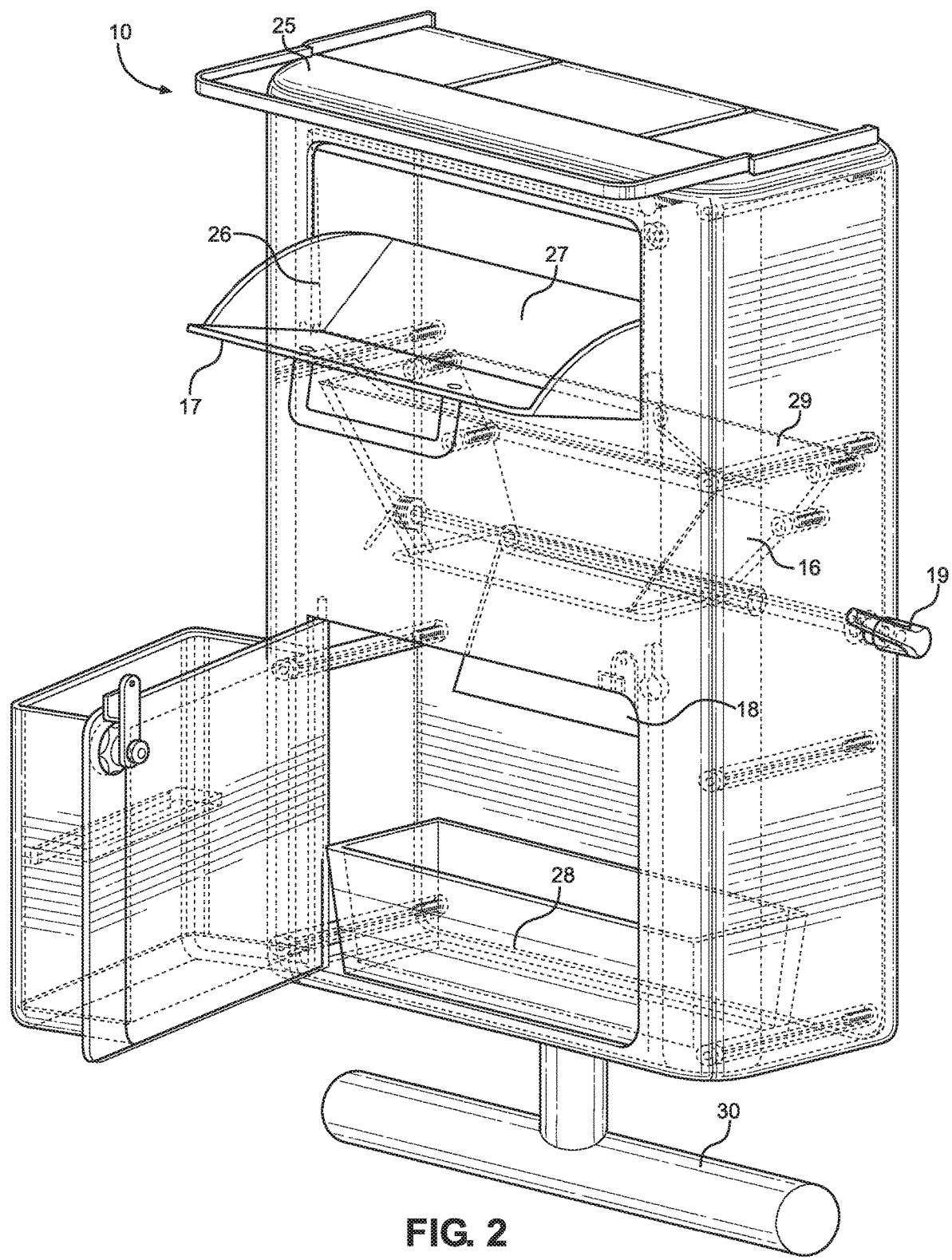
FIG. 2 shows a perspective view of an embodiment of the sanitary napkin disposal device.

Referring now to FIG. 2, there is shown a perspective view of an embodiment of the sanitary napkin disposal device. In the illustrated embodiment, the door 17 comprises a pair of door side walls 26 disposed on opposing edges of the door 17 and a door base 27 disposed between the pair of door side walls 26. The door base 27 is mounted in an angled manner, such that disposed items may slide off as the door 17 is placed into the closed positions. As such, disposed items placed in the door 17 will be more effectively guided into the upper opening 29 of the chute 16.

Additionally, in the illustrated embodiment, the sanitary napkin disposal device 10 further comprises a bin 28. The bin 28 is removably placed within the interior cavity of the housing. Specifically, the bin 28 rests on a top surface of the base of the housing. The bin 28 is positioned below the chute 16 such that disposed items will fall into the bin 28 after passing through the chute 16. Ideally, the chute 16 is of a diameter minimally less than the diameter of the housing, such that disposed items will fall into the bin 28 as opposed to the housing 11. This will reduce the risk of contaminants or germs from remaining in the housing after the bin 28 is removed and emptied.

Furthermore, in the illustrated embodiment, the sanitary napkin disposal device 10 comprises a paper roll holder 30 disposed on the base 12 of the housing 11. The paper roll holder 30 is configured to secure at least one paper roll thereon, such as a toilet paper roll. In the illustrated embodiment, the paper roll holder 30 is T-shaped in configuration, such that a pair of paper rolls can be stored thereon, wherein a paper roll is disposed on each arm of the paper roll holder 30.

Figure 3:
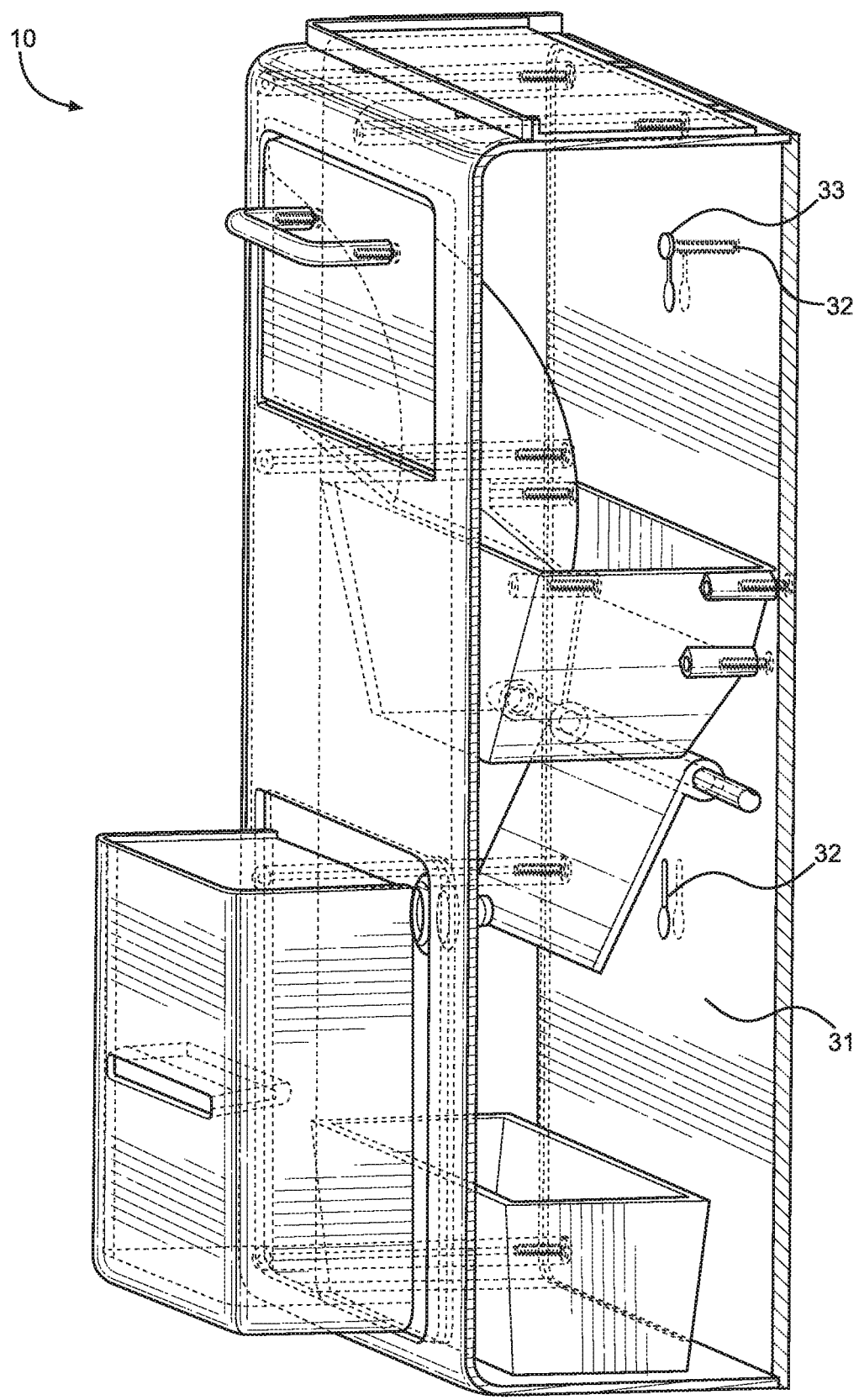
FIG. 3 shows a cutout view of an embodiment of the sanitary napkin disposal device.

Referring now to FIG. 3, there is shown a cutout view of embodiment of the sanitary napkin disposal device. In the illustrated embodiment, the sanitary napkin disposal device 10 comprises a rear sidewall 31. The rear sidewall 31, as shown, is substantially flat, such that the rear sidewall 31 can be placed in direct contact with a flat vertical surface, such as a wall. The rear sidewall 31 of the housing comprises a plurality of mounting holes 32. The plurality of mounting holes 32 are each configured to receive a fastener 33 therethrough. As such, the sanitary napkin disposal device 10 can be secured to the flat vertical surface chosen by the user. The plurality of mounting holes 32 may comprise any number of mounting holes for the desired purpose of securing the sanitary napkin disposal device 10 to the flat vertical surface. Furthermore, in the shown embodiment, each mounting hole of the plurality of mounting holes comprises an enlarged bottom section adapted to receive the head of a screw or nail.

Figure 4:
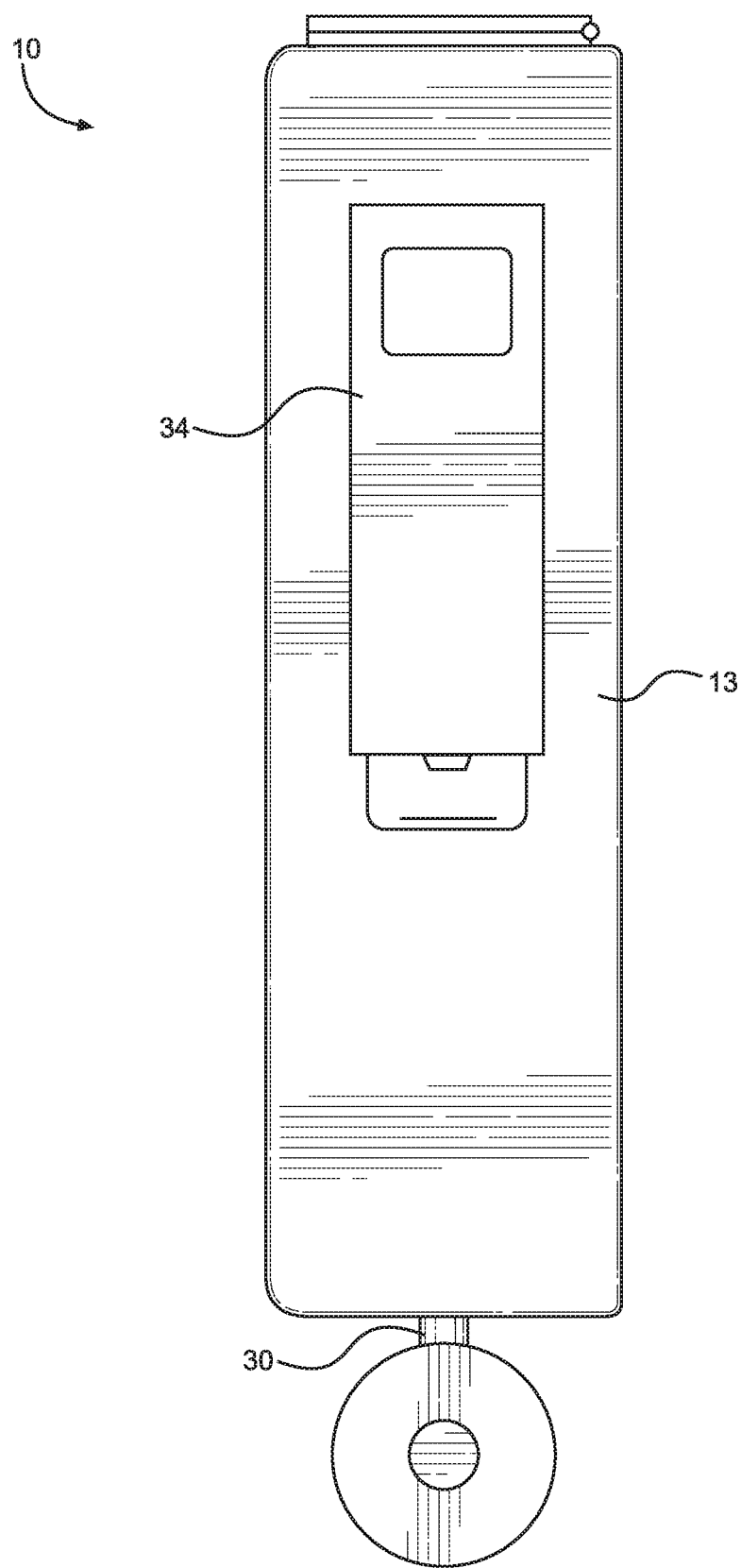
FIG. 4 shows a side view of an embodiment of the sanitary napkin disposal device.

Referring now to FIG. 4, there is shown a side view of an embodiment of the sanitary napkin disposal device. In the illustrated embodiment, the sanitary napkin disposal device 10 comprises a fluid dispenser 34 disposed on a sidewall 13 of the housing. The fluid dispenser 34 may be utilized to store and dispense a sanitizing fluid, such as hand sanitizer. As such, the user will have access to the sanitizing fluid after they are finished utilizing the sanitary napkin disposal device 10.

Figure 5:
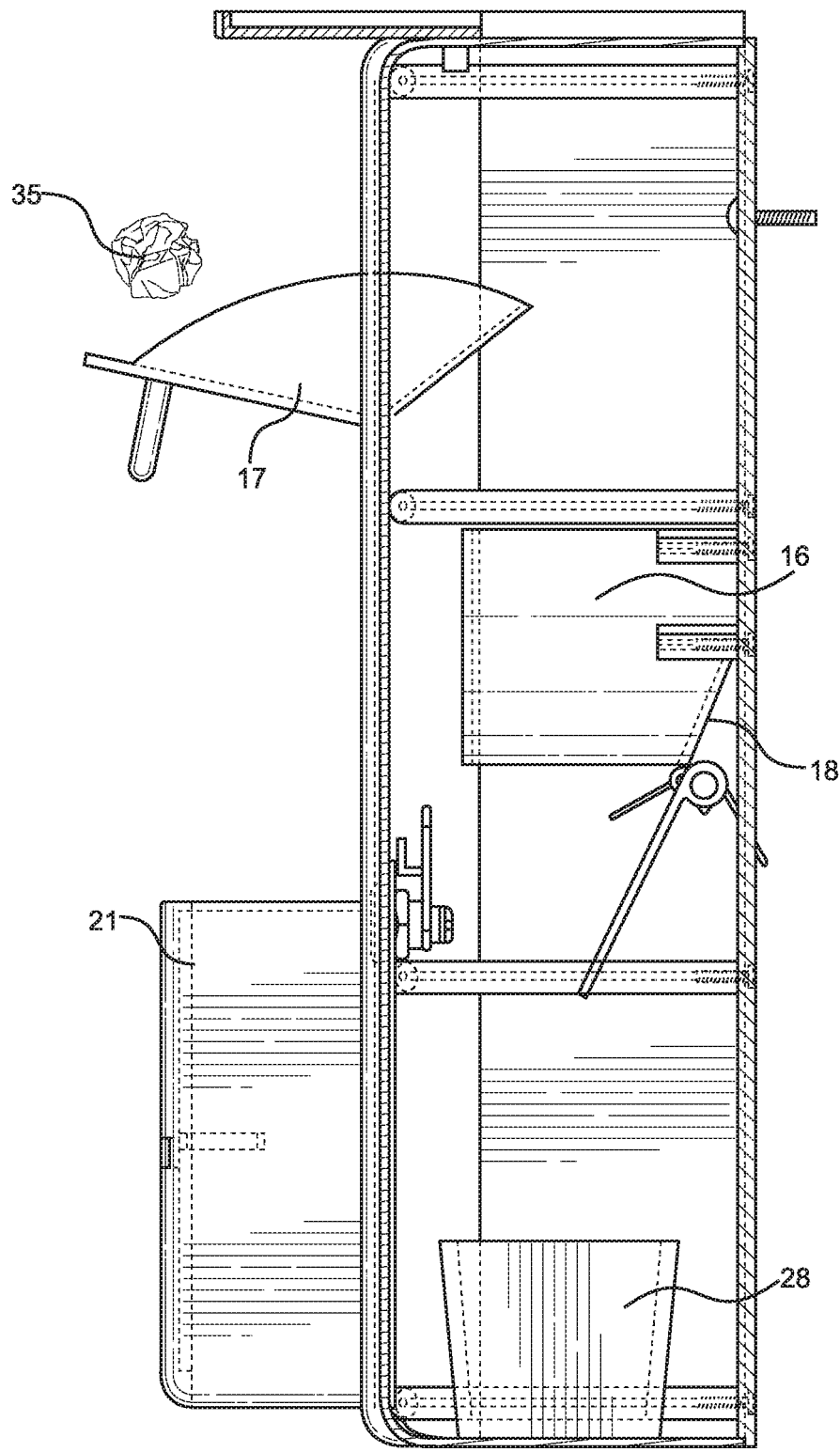
FIG. 5 shows a side cutout view of an embodiment of the sanitary napkin disposal device.

Referring now to FIG. 5, there is shown a side cutout view of an embodiment of the sanitary napkin disposal device. In use, a user may dispose of a sanitary napkin 35 or similar disposable object utilizing the sanitary napkin disposal device 10. The user will first place the sanitary napkin 35 through the door 17 while the door 17 is in the open position. From the door 17, the sanitary napkin 35 will pass through the chute 16. After passing through the chute 16, the sanitary napkin 35 will fall into the bin 28 where it will remain until removed through the waste door 21 on the front surface of the housing.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A sanitary napkin disposal device, comprising:
a housing defined by a base with a plurality of sidewalls extending upward therefrom and a top wall disposed upon the plurality of sidewalls;
the housing defining an interior volume;
an opening disposed on the housing, providing access to the interior volume;
the opening in operable connection with a chute;
a door disposed over the opening;
the door biased in a closed position over the opening;
an extendable platform disposed on the top wall of the housing.

2. The sanitary napkin disposal device of claim 1, wherein the chute comprises a trapdoor biased in a closed position, the trapdoor being operable via a trapdoor handle.

3. The sanitary napkin disposal device of claim 1, wherein the door comprises a handle thereon.

4. The sanitary napkin disposal device of claim 1, further comprising a waste door disposed on a bottom end of the housing.

5. The sanitary napkin disposal device of claim 4, wherein the waste door further comprises a box with a slot thereon.

6. The sanitary napkin disposal device of claim 4, wherein the waste door further comprises a lock thereon.

7. The sanitary napkin disposal device of claim 1, wherein the door comprises a pair of door sidewalls and a door base, configured to direct a disposed device into the chute.

8. The sanitary napkin disposal device of claim 1, wherein a bin is removably placed within the interior cavity of the housing, below the chute.

9. The sanitary napkin disposal device of claim 1, wherein a rear sidewall of the housing comprises a plurality of mounting holes, the plurality of mounting holes each configured to receive a fastener therethrough to secure the sanitary napkin disposal device to a targeted surface.

10. The sanitary napkin disposal device of claim 1, wherein a paper roll holder is disposed on an external surface of the base of the housing.

11. The sanitary napkin disposal device of claim 1, further comprising a fluid dispenser disposed on an external surface of the sidewall of the housing.

12. A sanitary napkin disposal device, comprising:
a housing defined by a base with a plurality of sidewalls extending upward therefrom and a top wall disposed upon the plurality of sidewalls;
the housing defining an interior volume;
an opening disposed on the housing, providing access to the interior volume;
the opening in operable connection with a chute;
wherein the chute comprises a trapdoor spring-biased in a closed position, the trapdoor being operable via a trapdoor handle;
a door disposed over the opening;
the door biased in a closed position over the opening;
a waste door disposed on a bottom end of the housing;
a bin removably placed within the interior cavity of the housing, below the chute.

13. A sanitary napkin disposal device, comprising:
a housing defined by a base with a plurality of sidewalls extending upward therefrom and a top wall disposed upon the plurality of sidewalls;
the housing defining an interior volume;
an opening disposed on the housing, providing access to the interior volume;
the opening in operable connection with a chute;
a door disposed over the opening;
the door biased in a closed position over the opening;
a waste door disposed on a bottom end of the housing;
wherein the waste door comprises a box with a slot thereon.

* * * * *